(12) United States Patent
Zakoshansky

(10) Patent No.: US 8,575,398 B2
(45) Date of Patent: Nov. 5, 2013

(54) NON-BARBOTAGE METHOD FOR OXIDATION OF HYDROCARBONS BY FORMING AND UTILIZING LIQUID PHASE THIN FILM

(75) Inventor: Vladimir Mikhailovitch Zakoshansky, Long Grove, IL (US)

(73) Assignee: Illa International, LLC, Reno, NV (US)

( * ) Notice: Subject to any disclaimer, the term of this patent is extended or adjusted under 35 U.S.C. 154(b) by 0 days.

(21) Appl. No.: 12/916,088

(22) Filed: Oct. 29, 2010

(65) Prior Publication Data

US 2011/0319668 A1    Dec. 29, 2011

Related U.S. Application Data

(60) Provisional application No. 61/256,857, filed on Oct. 30, 2009.

(51) Int. Cl.
    *C07C 409/00*    (2006.01)

(52) U.S. Cl.
    USPC ............ 568/572; 568/565; 568/568; 568/569

(58) Field of Classification Search
    None
    See application file for complete search history.

(56) References Cited

U.S. PATENT DOCUMENTS

| | | | |
|---|---|---|---|
| 5,292,941 | A | 3/1994 | Kigawa et al. |
| 7,393,984 | B1 | 7/2008 | Zakoshansky et al. |
| 2003/0092943 | A1 | 5/2003 | Fulmer et al. |
| 2006/0000781 | A1 | 1/2006 | Seidlitz et al. |
| 2007/0260093 | A1 | 11/2007 | Kuma et al. |

OTHER PUBLICATIONS

Japanese Patent Publication No. 2000-229938; Date of Publication: Aug. 22, 2000; 1 Page; English Abstract Only.
International Search Report for International Application No. PCT/US2010/054788; International Filing Date: Oct. 29, 2010; Date of Mailing: Jul. 25, 2011; 3 Pages.
Written Opinion of the International Searching Authority for International Applicaiton No. PCT/US2010/054788; International Filing Date: Oct. 29, 2010; Date of Mailing: Jul. 25, 2011; 3 Pages.
Zakoshansky "Phenomenology of Oxidation of a Cumene Feed Containing Hydroperoxide: I. Two Paths of Cumene Hydroperoxide Formation Reaction" Russian Journal of General Chemistry; vol. 81, No. 5; 2011; pp. 845-864.
Zakoshansky "Phenomenology of Oxidation of a Cumene Feed Containing Hydroperoxide: II. Limiting Hydroperoxide Concentration: True Causes and Approaches for Overcoming Thereof", Russian Journal of General Chemistry; vol. 81; No. 5; 2011; pp. 865-883.

*Primary Examiner* — Sudhakar Katakam
(74) *Attorney, Agent, or Firm* — Cantor Colburn LLP

(57) ABSTRACT

The purpose of the present invention is to provide an advantageous non-barbotage method for oxidation of hydrocarbons, that, when implemented in various embodiments thereof, provides significantly higher selectivity, a greater level of safety, lower capital costs, etc., than conventional oxidation processes utilizing the barbotage technique. The essence of the inventive non-barbotage oxidation process is ensuring that the oxidizing agent delivered to the process reactor undergoes continued contact only with exposed surfaces of the liquid phase of the hydrocarbons being oxidized configured as at least one of: formed liquid phase thin film(s), liquid phase continuous stream(s), and/or liquid phase globule (e.g., droplets, etc.) stream(s), preferably, with the surface area(s) of the exposed surface(s) being maximized to increase contact with an oxidizing agent being directed thereto, to ensure that the inventive oxidation reaction occurs at the border between liquid and gas phases, such that the oxidation reaction effectively occurs by way of contact of the oxidizing agent (e.g., oxygen) from the gas phase with exposed surface(s) of the liquid phase of the hydrocarbons being oxidized. The inventive non-barbotage oxidation process may be implemented in a single reactor, or in plural sequential reactors, and may be implemented both in a stand-alone configuration, and in combination with various conventional barbotage methods for oxidation of hydrocarbons.

17 Claims, 3 Drawing Sheets

NON-BARBOTAGE METHOD FOR OXIDATION OF HYDROCARBONS BY FORMING AND UTILIZING LIQUID PHASE THIN FILM

CROSS REFERENCE TO RELATED APPLICATION

This application is related to, and claims priority from, the co-pending commonly assigned provisional patent application entitled "Non-Barbotage Method for Oxidation of Aromatic Hydrocarbons", filed Oct. 30, 2009, which is hereby incorporated by reference herein in its entirety.

FIELD OF THE INVENTION

This invention relates to the field of the commercial manufacture of petrochemical synthesis products, and in particular, to a non-barbotage method for oxidation of hydrocarbons by formation and utilization of liquid phase thin film, both in a stand-alone configuration and in combination with various conventional barbotage methods for oxidation of hydrocarbons, that, when implemented in various embodiments thereof, is superior to all previously known barbotage-based hydrocarbon oxidation processes.

BACKGROUND OF THE INVENTION

Without exception, various existing commercial processes for oxidation of hydrocarbons (e.g., aromatic hydrocarbons such as cumene hydroperoxide (hereinafter "CHP"), etc.), by their very technical configuration comprise barbotage-based processes, in which an oxidizing agent (typically air or air-oxygen) is passed through a layer of the liquid phase of the hydrocarbons being oxidized by way of barbotage (i.e., by formation and movement of air bubbles therethrough).

Accordingly, the conventional oxidation reactors are almost completely filled with the liquid phase which comprises a mixture of the product being oxidized, and of oxidation reaction by-products (e.g., hydroperoxides and by-products). The gas phase—the air delivered to the reactor, and the off-gas exiting the reactor (having a lower oxygen concentration)—takes up a relatively small portion of the surrounding liquid phase (e.g., approximately 8% of volume), and therefore typically only occupies approximately 15% of the overall reactor volume. Air (i.e., the gas phase) is typically fed through the bottom portion of the reactor through a bubble distributor component configured to minimize the size of the air bubbles passing therethrough.

As the air bubbles rise upward through the liquid phase (which almost completely fills the reactor), they transfer the gas phase oxygen ($O_2^{gas}$) to the liquid phase of the products being oxidized, while simultaneously being dissolved therein. Unfortunately, this approach, involving barbotage of air through a liquid phase, does not forbid an increase of the total surface area of the gas phase bubbles, and accordingly, prohibits the desirable increase in the speed of the reaction of formation of the hydroperoxide product, and thus also limits the ability to raise process selectivity, at least for the following reasons:

(1) The high speed at which the air bubbles rise upward through the height of the reactor, and
(2) Strict safety protocols regarding limitations of oxygen concentration in the off-gas.

In any barbotage-type oxidation process, oxygen ($O_2^{gas}$), is primarily expended in the course of formation of reaction by-products, and is only partially expended in formation of the desired product—hydroperoxide. Moreover, in barbotage-type oxidation processes, at least a portion of the oxygen ($O_2^{gas}$) is actually expended in the course of formation of undesirable reaction by-products that in fact serve as oxidation reaction inhibitors.

All of the above factors, in concert, lead to an insufficient level of conversion of the hydrocarbon being oxidized, and significantly lower process selectivity. As a result, previously known commercial processes have been unable to achieve a sufficiently high hydroperoxide concentration and selectivity in their oxidation reaction output products. For example in commercial barbotage processes involving oxidation of cumene, the maximum obtained concentration of the CHP product does not exceed 35% mass, while in processes involving oxidation of sec-butylbenzol, the concentration of the obtained hydroperoxide does not exceed 8%-10% mass. However, without exception, even if an increase in the conversion of the initial hydrocarbons (and, correspondingly, an increase in hydroperoxide concentration), is somehow obtained, it is only at the expense of considerable decrease in process selectivity, to a level practically unacceptable for commercial processes.

Irrespective of the chemical composition of the product being oxidized, the differences between existing barbotage-based oxidation processes are not sufficient to be considered as fundamental. For example, in a process of oxidizing of cumene into CHP, various barbotage-based processes comprise the following variations/differences therebetween:

(1) Differences in process temperature:
 (a) low temperature process: from 80° C. to 95° C., which predetermines and necessitates the use of enormous reactors in process implementation;
 (b) medium temperature process: from 95° C. to 115° C.; and
 (c) high temperature process: from 115° C. to 130° C.;
(2) Differences in pressure implemented in process reactors:
 (a) low pressure: from 1.2 to 1.5 atm.;
 (b) medium pressure: from 4 to 5 atm.; and
 (c) high pressure: from 6 to 7 atm.
(3) Differences in alkaline agent being utilized:
 (a) NaOH or a mixture of NaOH with $NH_4OH$—the so-called "dry oxidation process"; and
 (b) Water solution of $Na_2CO_3$ and $Na_2CO_3$ together with $NH_4OH$—the so-called "wet (or water-emulsion) oxidation process".

The maximum selectivity that has been achieved in practice to date in barbotage-type cumene oxidation processes has not exceeded about 95% mol. with conversion of cumene not exceeding about 30% mol.—moreover, further increases in conversion of cumene (and correspondingly, in the concentration of CHP), has lead to a catastrophic increase in formed amounts of undesirable by-products, and a drop in process selectivity.

In oxidation of other hydrocarbons, for example, aromatic hydrocarbons, such as ethylbenzol and sec-butylbensol, the conditions are much more severe—the reaction temperature and pressure are higher, and the alkaline agent is delivered to the reaction is much higher than in cumene oxidation processes, while the ranges of the above-noted key process parameters are much more narrow.

Accordingly, the essence of conventional commercial technologies remains unchanged—namely, the barbotage of air through a liquid phase of the hydrocarbons being oxidized, with the hydrocarbons' inexorably low conversion in view of the significant inhibition of the process by the resulting reaction by-products. And, as was noted above, the key commonality between all previously known barbotage-based processes is their inevitably low conversion of the hydroperoxides being oxidized, and their fundamental inability to obtain hydrocarbons having practically no reaction byproducts.

It would thus be desirable to provide a process of oxidation of hydrocarbons, that enables significantly higher selectivity, a greater level of safety, lower capital costs, etc., than conventional oxidation processes utilizing the barbotage technique.

SUMMARY OF THE INVENTION

The purpose of the present invention is to provide an advantageous non-barbotage method, both in a stand-alone configuration, and in combination with a conventional barbotage method (with reactors utilizing the different methods being positioned sequentially), for oxidation of hydrocarbons, that, when implemented in various embodiments thereof, is superior in many ways to all previously known barbotage-based hydrocarbon (and in particular, aromatic hydrocarbon) oxidation processes. Specifically, the inventive process provides significantly higher selectivity, a greater level of safety, lower capital costs, etc., than conventional oxidation processes utilizing the barbotage technique.

The essence of the inventive non-barbotage oxidation process is ensuring that the oxidizing agent delivered to the process reactor undergoes continued contact only with exposed surfaces of the liquid phase of the hydrocarbons being oxidized (such as at least one of: formed liquid phase thin film(s), liquid phase thin continuous stream(s), and/or liquid phase globule (e.g., droplets, etc.) stream(s)), preferably, with the surface area(s) of the exposed surface(s) being maximized to increase contact with an oxidizing agent being directed thereto, to ensure that the inventive oxidation reaction occurs at the border between liquid and gas phases, such that the oxidation reaction effectively occurs by way of contact of the oxidizing agent (e.g., oxygen) from the gas phase with the exposed surface(s) of the liquid phase of the hydrocarbons being oxidized.

For example, in one embodiment of the present invention, the liquid phase thin film may be specially formed on one or more pre-configured surfaces provided in the reactor, and ensures that the inventive oxidation reaction occurs at the border between liquid and gas phases, such that the oxidation reaction effectively occurs by way of contacting the oxidizing agent (e.g., oxygen) from the gas phase with the developed outer surface of the thin film liquid phase of the hydrocarbons being oxidized.

In other embodiments of the present invention, one or more liquid phase hydrocarbon streams (which may be continuous flowing stream(s), and/or stream(s) of globules (e.g., droplets, drops, etc.), may be generated to maximize the exposed hydrocarbons liquid phase surface area for contact with the gas phase oxidizing agent (e.g., oxygen) being directed thereto.

Advantageously, in various embodiments thereof, the inventive non-barbotage oxidation process may be implemented in a single reactor, or in plural reactors in a cascade configuration—with sequentially positioned reactors. In various alternate embodiments of the present invention, the inventive process may be implemented in combination with one or more conventional barbotage-type oxidation processes by use of multiple sequential reactors, with at least one non-barbotage type reactor being configured to implement at least one embodiment of the inventive non-barbotage method of hydrocarbon oxidation by forming and utilizing thin liquid phase film, and at least one other barbotage type reactor being configured to implement at least one barbotage-type hydrocarbon oxidation. In a preferred embodiment of the present invention, the at least one barbotage reactor is positioned following the at least one non-barbotage reactor to maximize overall process selectivity. However, any sequence, any number and/or combination of non-barbotage type and barbotage type reactors may be utilized as a matter of choice without departing from the spirit of the present invention.

Furthermore, to further improve process selectivity, in a preferred embodiment of the present invention, a step of removal of reaction inhibitors (e.g., impurities) may be provided at the output of one or more of the process reactors.

The various features of novelty which characterize the invention are pointed out with particularity in the claims appended to and forming a part of this specification. For a better understanding of the invention, its operating advantages and specific objects obtained by its use, reference should be had to the accompanying drawings and descriptive matter in which there is illustrated and described a preferred embodiment of the invention.

BRIEF DESCRIPTION OF THE DRAWINGS

In the drawings, wherein like reference characters denote corresponding or similar elements throughout each figure.

DETAILED DESCRIPTION OF PREFERRED EMBODIMENTS

Figure 1:
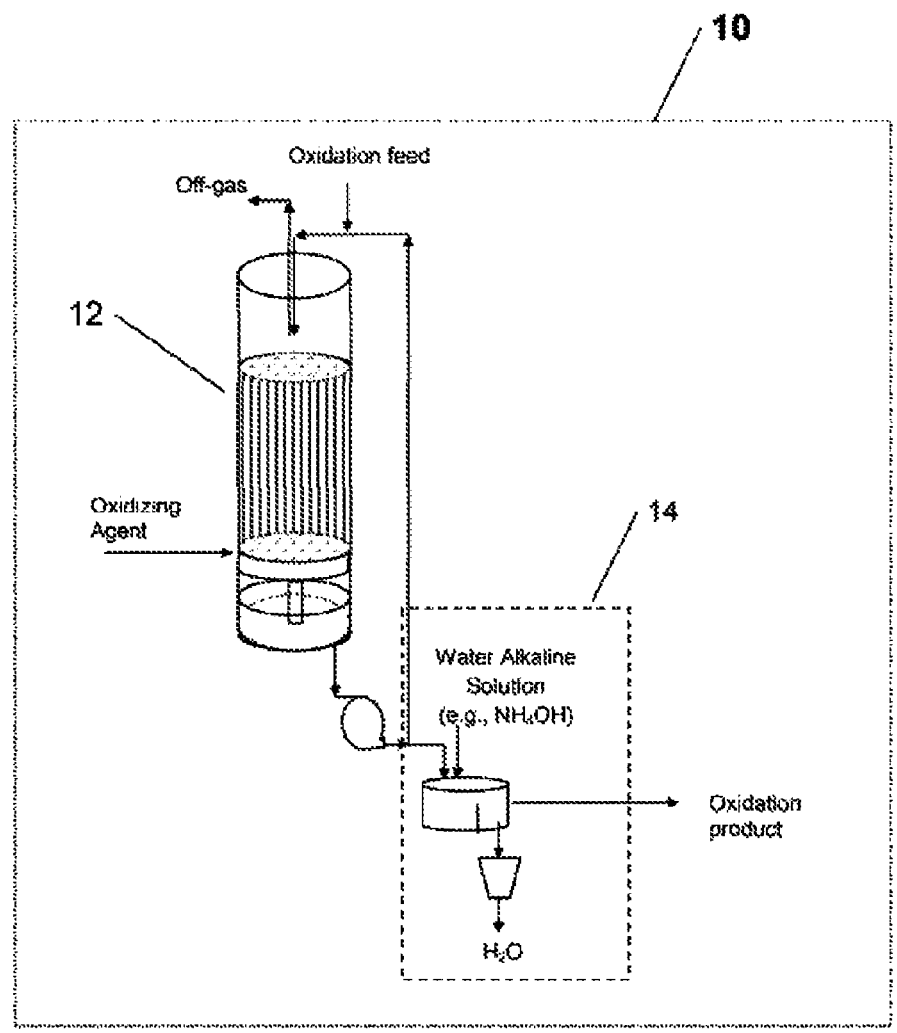
FIG. 1 is a schematic simplified flow diagram of an exemplary first embodiment of the inventive method for a non-barbotage method for oxidation of hydrocarbons, implemented in a single reactor, shown with an optional reaction inhibitor system at the output thereof.

The present invention is aimed at eliminating the disadvantages of all previously known barbotage-based hydrocarbon oxidation processes, and provides, an advantageous non-barbotage method for oxidation of hydrocarbons, that, when implemented in various embodiments thereof, is superior in many ways to all previously known barbotage-based hydrocarbon (and in particular aromatic hydrocarbon) oxidation processes. Specifically, the inventive process provides significantly higher selectivity, a greater level of safety, lower capital costs, etc., than conventional hydrocarbon oxidation processes utilizing the barbotage technique.

The essence of the inventive non-barbotage oxidation process is ensuring that the oxidizing agent ($O_2^{gas}$) that is delivered to the process reactor, undergoes continued contact only with an exposed thin surface region of the liquid phase of the hydrocarbons being oxidized. It should be noted that the specific composition of the oxidizing agent may be selected as a matter of design choice, as long as it includes air oxygen (or equivalent thereto). Thus for example, the oxidizing agent composition that is used in accordance with the present invention, may include, but is not limited to, air oxygen available in vicinity of the reaction, a mixture of air oxygen and additional nitrogen added thereto, and a mixture of air oxygen and additional oxygen added thereto.

It should also be noted that the inventive process may be readily utilized with a virtually any hydrocarbon or equivalent in the oxidation feed thereto, that, by way of example may include, but that is not limited to:

(1) aromatic hydrocarbons, such as one or more of: cumene, monoalkyl-substituted hydrocarbons, dialkyl-substituted hydrocarbons, hydrocarbons of a general formula $C_6H_5$-Alk, wherein Alk is a methyl, ethyl, n-propyl, iso-propyl, n-butyl, or sec-butyl group, etc.;

(2) aliphatic hydrocarbons, such as hydrocarbons of a general formula $C_4H_{10}$ to $C_{15}H_{32}$; and (3) alicyclic hydrocarbons, such as alkylcyclohexane.

Advantageously, in accordance with the present invention, if the hydrocarbon feed being used comprises aromatic hydrocarbons, it is preferable to select aromatic hydrocarbons that facilitate and enable production of corresponding desired hydroperoxide(s). For example, referring to Scheme 1:

(1) To produce the hydroperoxide oxidation output that, as its primary component, includes cumene hydroperoxide (CHP), cumene may be used as the aromatic hydrocarbon;

(2) To produce the hydroperoxide oxidation output that, as its primary component, includes diisopropylbenzene dihydroperoxide, diisopropylbenzene may be used as the aromatic hydrocarbon;

(3) To produce the hydroperoxide oxidation output that, as its primary component, includes ethylbenzene hydroperoxide, ethylbenzene may be used as the aromatic hydrocarbon;

(4) To produce the hydroperoxide oxidation output that, as its primary component, includes sec-butylbenzene hydroperoxide, sec-butylbenzene may be used as the aromatic hydrocarbon;

(5) To produce the hydroperoxide oxidation output that, as its primary component, includes toluene hydroperoxide, toluene may be used as the aromatic hydrocarbon;

(6) To produce the hydroperoxide oxidation output that, as its primary component, includes n-propylbenzene hydroperoxide, n-propylbenzene may be used as the aromatic hydrocarbon; and (7) To produce the hydroperoxide oxidation output that, as its primary component, includes n-butylbenzene hydroperoxide, n-butylbenzene may be used as the aromatic hydrocarbon.

Scheme 1

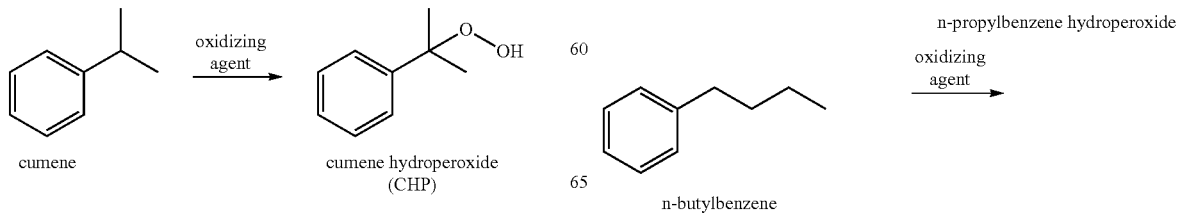

-continued

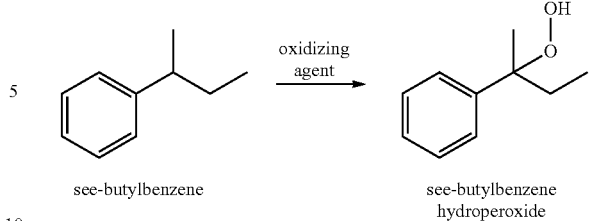

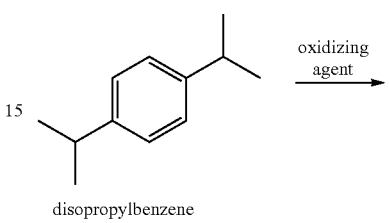

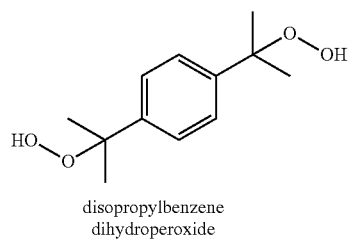

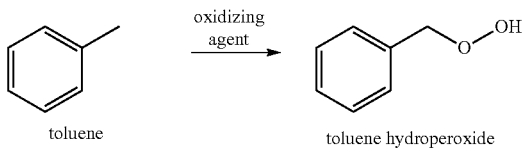

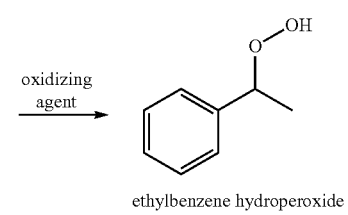

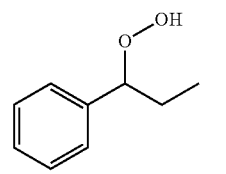

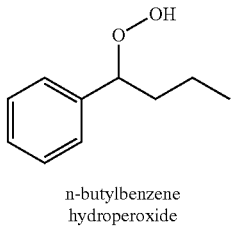

n-butylbenzene hydroperoxide

In one embodiment of the present invention, described in greater detail below, the hydrocarbons liquid phase may be artificially formed as a thin film on one or more pre-configured "contact" surface(s) provided in the reactor, and as a result of such contact, the gas phase oxygen ($O_2^{gas}$) reacts with the hydrocarbon with formation of hydroperoxide at the border of the separation between the liquid and gas phases, that is created by the thin liquid phase film.

In other embodiments of the present invention, one or more liquid phase hydrocarbon streams (which may be continuous flowing stream(s), and/or stream(s) of globules (e.g., droplets, drops, etc.), may be generated to maximize the exposed hydrocarbons liquid phase surface area for contact with the gas phase oxidizing agent (e.g., oxygen, air, etc.) being directed thereto.

Essentially, the novel oxidation reaction effectively occurs by way of contact of oxygen from the gas phase with a thin exposed outer surface of the liquid phase of the hydrocarbons being oxidized. Therefore, in contrast to all previously known hydrocarbon oxidation process solutions, the inventive process takes place without passing the oxidizing agent (e.g., oxygen, air, etc.) though the primary hydrocarbons liquid phase by way of barbotage. Accordingly, because the inventive process does not utilize the step of air barbotage through the primary portion of the liquid phase, the novel oxidation reaction is conducted virtually only by $O_2^{gas}$ molecules at the border of the separation between the liquid and gas phases, that do not practically lead to formation of undesirable reaction by-products, reaction inhibitors, or any decelerants of the primary CHP formation reaction, that are capable of inhibiting or even stopping the oxidation reaction.

In one exemplary embodiment of the present invention, the thin liquid phase film is created on at least one rigid surface provided in the reactor, for example, by way of continuous delivery of the product being oxidized thereto, from the lower portion of the reactor. Preferably, the total surface area of such rigid surfaces, suitable for thin liquid phase film formation thereon, should be maximized to facilitate the desired magnitude of concentration of obtained hydroperoxide, and to correspondingly increase the productivity of the reactor, or the reactor cascade.

In other embodiments of the present invention, the thin liquid phase film may be formed by way of one or more liquid phase hydrocarbon streams (which may be continuous flowing stream(s), and/or stream(s) of globules (e.g., droplets, drops, etc.), that may be generated to maximize the exposed hydrocarbons liquid phase surface area for contact with the gas phase oxidizing agent (e.g., oxygen) being directed thereto.

It should therefore be noted that the manner of formation, and/or configuration, of the thin liquid phase film of the hydrocarbons being prepared for maximized surface area contact with the oxidizing agent (i.e., whether formed on one or more rigid surfaces in the reactor(s), directed as a one or more continuous (and preferably thin) streams, directed as one or more globule (e.g., droplet) streams, or by any other means), may be selected as a matter of design choice without departing from the spirit of the present invention, as long as the process of the formation of the desired reaction product—CHP, occurs at the border of the separation between the liquid and gas phases, with the participation of the gas phase oxygen ($O_2^{gas}$). Therefore, it should be noted that all references herein to "thin film" of the hydrocarbons liquid phase, include, but are not limited to, any hydrocarbon liquid phase configurations and any combinations thereof (e.g., surface-formed film(s), continuous flowing stream(s), globule stream(s), etc.) that are thin, but that have maximized surface area(s) for contact with the oxidizing agent.

Advantageously, in various embodiments thereof, the inventive non-barbotage oxidation process may be implemented in a single reactor, or in plural reactors in a cascade configuration. Referring now to FIG. 1, an exemplary first embodiment of the novel process utilizing the inventive method is shown as a process 10, utilizing a single reactor 12. The inventive oxidation reaction of the process 10 may be conducted in the reactor 12 isothermally or non-isothermally (for example, adiabatically), as a matter of choice without departing from the spirit of the invention.

Figure 2:
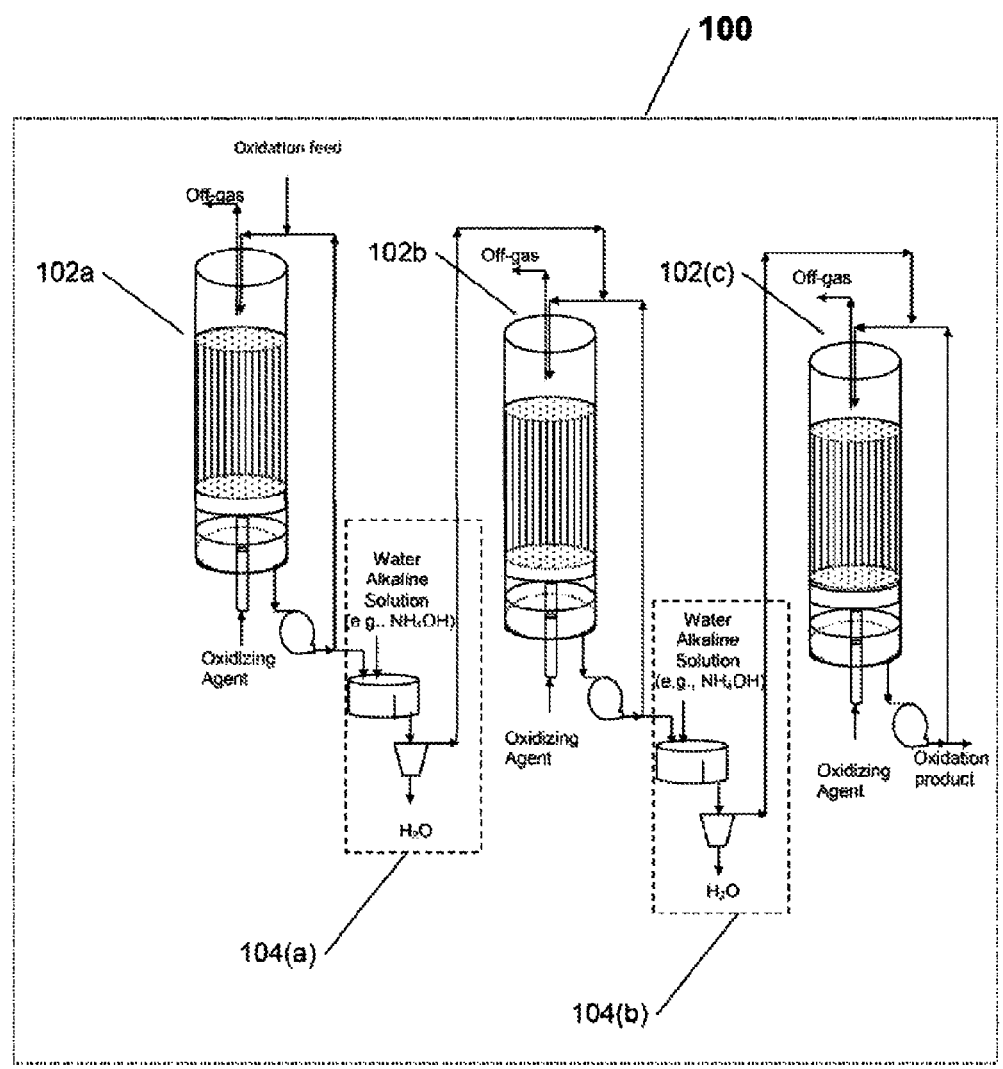
FIG. 2 is a schematic simplified flow diagram of an exemplary second embodiment of the inventive method for a non-barbotage method for oxidation of hydrocarbons, implemented in a cascade of plural reactors, shown with optional reaction inhibitor systems at the output of several reactors of the reactor cascade.

Referring now to FIG. 2, an exemplary second embodiment of the novel process utilizing the inventive method is shown as a process 100, utilizing a cascade of plural sequential reactors (shown as three reactors 102a, 102b, and 102c, by way of example only, and not as any limitation of the number of reactors that may be used in accordance with the present invention). Advantageously, in a plural sequential reaction embodiment of the present invention, the novel oxidation process may be conducted isothermally in all plural reactors, non-isothermally (for example, adiabatically) in all plural reactors, or conducted in a predetermined combination of one or more isothermally configured reactors and non-isothermally (for example, adiabatically) configured reactors. Therefore, by way of example, in various exemplary embodiments of the present invention, as a matter of choice, and without departing from the spirit of the invention, the novel oxidation reaction of the process 100 may be conducted in one or more of the following configurations:

(1) isothermally in each reactor 102, 104,
(2) adiabatically in each reactor 102, 104, or
(3) isothermally in one of the reactors 102, 104, and adiabatically in the other of the reactors 102, 104.

It should also be noted, that in alternate embodiments of the present invention, any of the different embodiments of the present invention can be readily combined with, and/or otherwise integrated into, any traditional barbotage-based oxidation process, without departing from the spirit of the invention, such that a resulting combined process may comprise oxidation that is conducted both under non-barbotage oxidation utilizing gas phase oxygen ($O_2^{gas}$) methodology of the present invention, as well as under traditional barbotage oxidation utilizing delivery of liquid phase oxygen ($O_2^{liquid}$) through the oxidation products, which may be implemented either in separate sequential reactors, or in a separate designated reactor.

In a preferred exemplary embodiment of the above-mentioned inventive combined process, to maximize overall process selectivity, at least one reactor implementing at least one corresponding conventional barbotage-based process (hereinafter "at least one barbotage process reactor"), may be positioned following the at least one reactor implementing at least one embodiment of the inventive non-barbotage method of hydrocarbon oxidation by forming and utilizing thin liquid phase film (hereinafter "at least one non-barbotage process reactor").

Figure 3A:
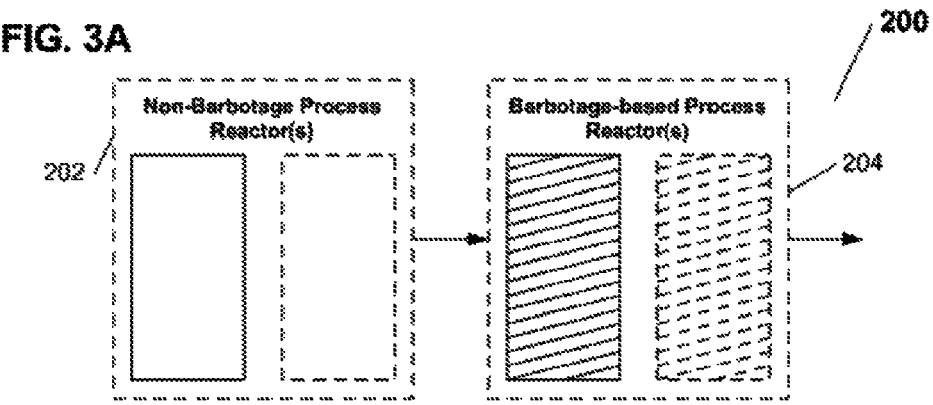
FIGS. 3A to 3C are schematic simplified block diagrams of exemplary alternate embodiments of the present invention in which at least one of the inventive process embodiments of FIGS. 1 and/or 2 above, is combined with at least one conventional barbotage-based process, that are implemented in various configurations of series of plural sequential reactors.
Figure 3B:
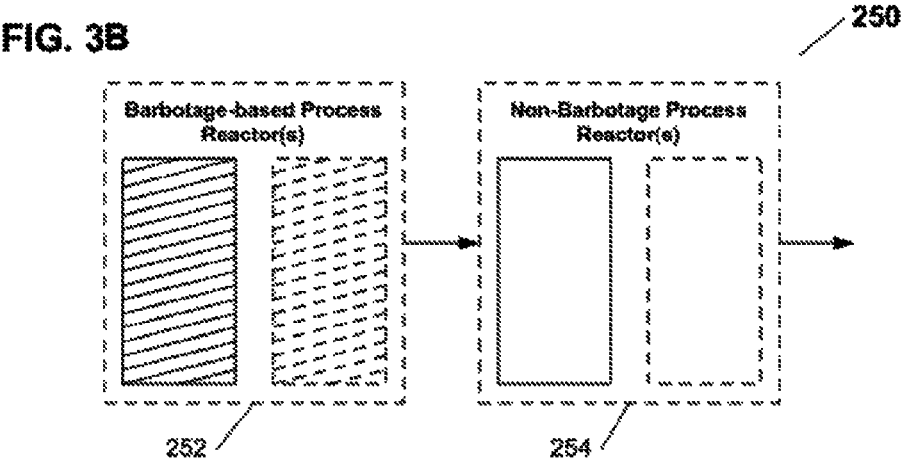
Figure 3C:
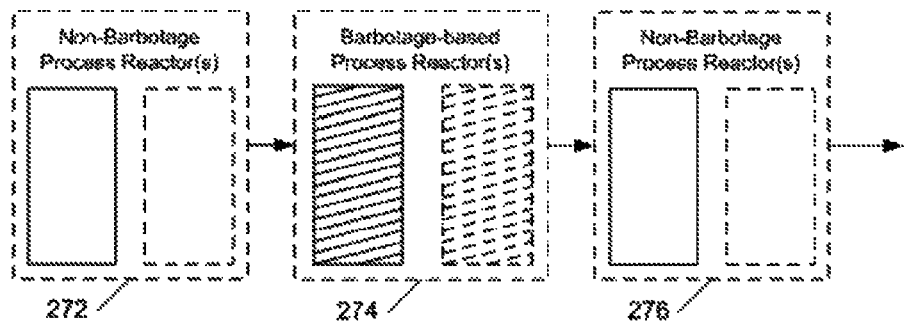

For example, referring now to FIG. 3A, in a combined oxidation process 200, the at least one barbotage process reactor 204 is positioned following the at least one non-barbotage process reactor 202 (which may, for example, implement at least one of the process 10 of FIG. 1, and/or of the process 100 of FIG. 2). However, any sequence, any number and/or combination of non-barbotage type and barbotage type reactors may be utilized as a matter of choice without departing from the spirit of the present invention. For example, referring now to FIG. 3B, an alternate exemplary embodiment of the present invention, is shown as a process 250, in which at least one barbotage process reactor 252 is positioned before at least one non-barbotage process reactor 254, while referring to FIG. 3C, another alternate exemplary embodiment of the present invention, is shown as a process 270, in which at least one non-barbotage process reactor 272 is sequentially followed by at least one barbotage process reactor 274, which is then sequentially followed by another at least one non-barbotage process reactor 276. Similarly, as is noted above in connection with FIG. 2, in the various inventive process embodiments of FIGS. 3A-3C (i.e. processes 200, 250, 270), the novel oxidation process may be conducted isothermally in all plural reactors, non-isothermally (for example, adiabatically) in all plural reactors, or conducted in a predetermined combination of one or more isothermally configured reactors and non-isothermally (for example, adiabatically) configured reactors.

In an alternate embodiment of the present invention, that may be implemented in the process 10 (FIG. 1), 100 (FIG. 2), etc., the inventive non-barbotage oxidation process (e.g. 10, 100) may adapted to utilize one or more conventional barbotage techniques in conjunction therewith, within one or more of the process reactors in which the inventive process is implemented, by passing the oxidizing agent (e.g., oxygen, air, etc.) by barbotage, e.g. by way of generating and directing air bubbles of the oxidizing agent through at least a portion of the non-film hydrocarbon liquid phase volume that collects in a predefined region (e.g., bottom) of the process reactor, e.g., during operation of the inventive process. The oxidizing agent air bubbles may be generated by any desired barbotage technique selected as a matter of choice.

Preferably, in various embodiments of the present invention, the quantity, in the lower part of each reactor, of the product being oxidized, is minimized such that it is sufficient substantially only for:
(1) the formation of thin film(s), within the reactor, of the liquid phase of the product being oxidized, having maximum possible surface area for contact with the oxidizing agent, and
(2) direction of a portion of the oxidized product collected from a bottom section of a reactor into:
  (a) a subsequent process stage for processing the obtained hydroperoxide—when the inventive process is implemented in a single reactor (e.g., reactor 12 of the process 10 in FIG. 1) in which the oxidation reaction takes place until the desired hydroperoxide concentration is reached in the output product; OR
  (b) the next sequential process reactor, and, after the last reactor in the reactor sequence, into the subsequent process stage for processing the obtained hydroperoxide—when the inventive process is implemented in a cascade of plural sequential reactors (e.g., reactors 102a, 102b, and then 102c, of the process 100 in FIG. 2); OR
  (c) the next sequential barbotage process reactor, in the embodiment of the present invention that utilizes a combination of the inventive non-barbotage oxidation process with a conventional barbotage oxidation process implemented in sequential reactors, in which a barbotage process reactor follows a non-barbotage process reactor (such as in the exemplary process 250 of FIG. 3A).

Furthermore, preferably, in various embodiments of the present invention, prior to being delivered for irrigation of the substantially rigid surface(s) provided in the reactors (e.g., reactors 12, 102a, 102b, etc.), in order to form the desirable thin liquid phase film and the contact surface of the liquid phase with a stream of the oxidizing agent containing gas phase oxygen ($O_2^{gas}$), the obtained oxidate is subjected to special processing for removal of oxidation reaction inhibitors therefrom, to prevent deceleration of the main reaction of hydroperoxide formation, and to minimize formation of undesirable by-products. Such oxidate processing/treatment can be conducted utilizing any of a wide variety of applicable techniques and typically involves the steps of:
(1) contacting the oxidate with an alkaline agent (e.g., inhibitors can be removed from the oxidate through its treatment using an aqueous solution of ammonia or any another alkaline agent),
(2) washing of the oxidate with water, and
(3) and removal of water (water can effectively be separated from the oxidized hydrocarbon using any common applicable method/technique (e.g., by use of decantation, cyclonage, coalescing filter, or by membrane-based separation).

Clearly, the fact that the volume of the oxidate in various embodiments of the present invention is tens of times smaller than oxidate volume in barbotage-type reactors, results in a much more effective and economic process for removal of reaction inhibitors from the obtained oxidate.

This preferable, but completely optional, inhibitor removal procedure that may be implemented in different embodiments of the present invention, is shown as an optional inhibitor removal sub-process 14 in FIG. 1, and as optional inhibitor removal sub-processes 104a and 104b in FIG. 2. If such at least one inhibitor removal sub-process is implemented in the inventive process, then the oxidate collected in the bottom of each reactor of the cascade resulting from the oxidation reaction therein, is drawn off from each reactor (e.g. reactor 10, or 102a or 102b), for removal of inhibitors therefrom (at inhibitor removal sub-process(es) 14, 104a, or 104b), and is further recycled for refluxing the baffles installed in the reactor while the inhibitor-free oxidate flows to a subsequent reactor of the cascade. The aqueous layer that is produced at the inhibitor removal step, is then partially recirculated to the same step, while its remaining portion is removed from the process.

As is noted above, the inventive oxidation process can either include or exclude the optional inhibitor removal step, or in the case of a cascade of plural reactors implementation, may only include the inhibitor removal step at the output of only some of the reactors in the sequence. However, regardless of the fact that the magnitude of process selectivity is somewhat lower in the inventive process embodiments implemented without a step of inhibitor removal, even such lower magnitude is greater as than the magnitude of selectivity possible in barbotage processes implemented in reactors using air bubbling through an oxidation mixture.

The oxidizing agent (e.g., air, etc.) is delivered to each process reactor in such a manner, as to pass over the surface area(s) of the thin film(s) of the liquid phase of the product, being oxidized unidirectionally and/or as a countercurrent. Therefore, depending on the physical configuration of each reactor, and based on the manner in which the substantially rigid surfaces configured for thin liquid phase film formation thereon are disposed within the reactor (e.g., as baffles, etc.), or if the thin liquid phase films are formed by way of continuous thin liquid phase streams and/or globule liquid phase stream(s), the oxidizing agent may be delivered through the top, bottom, or side section of the reactor.

In various embodiments of the present invention, the lower and upper limits of the desirable reactor temperature are determined both by the chemical structure (and corresponding reactivity) of the hydrocarbon selected for oxidation, and also by the predetermined desired concentration of the hydroperoxide at the outlet of the reactor system. Nevertheless, the temperature in the process reactor (or in reactors, if a reactor cascade is being utilized) in oxidation reactions of various hydrocarbons should be minimized to thereby hinder the formation of oxidation reaction inhibitors and to reduce the formation of undesirable by-products. By way of example only, and not as a limitation to the temperature ranges in which the various embodiments of the present invention are capable of readily operating, the inventive process 10 (FIG. 1), and/or 100 (FIG. 2), may be conducted under a temperature in a range from about 20° C. to about 150° C.

The pressure in the process reactor (or in reactors, if a reactor cascade is being utilized) in oxidation reactions of various hydrocarbons should be minimized to thereby maintain the lowest possible concentration of dissolved oxygen $O_2^{liquid}$ in the oxidate that is disposed in the lower section of each reactor, and in the products configured as thin liquid phase film (e.g., by formation on the substantially rigid surfaces provided in the reactor, as continuous thin liquid phase streams, and/or as globule liquid phase stream(s), or as equivalents thereof). By way of example only, and not as a limitation to the pressure ranges in which the various embodiments of the present invention are capable of readily operating, the inventive process 10 (FIG. 1), and/or 100 (FIG. 2), may be conducted under a pressure in a range from about 0.5 to about 15 atmospheres.

The concentration of the hydroperoxide at the output of the process reactor (or of the last reactor in the cascade sequence, if a reactor cascade is being utilized) in oxidation reactions of various hydrocarbons, is maximized, and, depending on the structure of the hydrocarbon being oxidized, and its corresponding reactivity, is maintained at a sufficiently high level to ensure the desired hydroperoxide yield. For example in some exemplary embodiments of the present invention, the oxidate product of the inventive reaction may comprise at least about 10% mass of hydroperoxides, while in other exemplary embodiments of the present invention, the oxidate product may comprise between about 5% to about 85% mass of hydroperoxides.

The overall surface areas of the thin liquid phase films at which the oxidation of the hydrocarbons by gas phase oxygen ($O_2^{gas}$) takes place, is preferably maximized to provide the necessary level of hydroperoxide concentration, and correspondingly, to achieve the required productivity for the reactor (or reactor cascade) with respect to the received hydroperoxide.

Advantageously, with oxidation of hydrocarbons at the border of the separation between the liquid and gas phases, with the participation of the gas phase oxygen ($O_2^{gas}$) in any thin film hydrocarbon liquid phase configuration of the present invention (e.g., surface-formed film(s), continuous flowing stream(s), globule stream(s), etc.), the hydrocarbon conversion level is at about 80%, while process selectivity achieves about 99.5% mol.—i.e. results that are vastly superior to any heretofore known commercial barbotage-based hydrocarbon oxidation process.

Thus, while there have shown and described and pointed out fundamental novel features of the invention as applied to preferred embodiments thereof, it will be understood that various omissions and substitutions and changes in the form and details of the devices and methods illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

I claim:

1. A method for oxidation of a hydrocarbon into a corresponding hydroperoxide, implemented in at least one non-barbotage process reactor, said method comprising the steps of:
   (a) generating a liquid phase reaction component comprising said hydrocarbon, said liquid phase reaction component further comprising:
   at least one exposed surface, and
   at least one of
   a liquid phase film disposed on a rigid surface,
   a liquid phase continuous stream, and
   a liquid phase globule stream comprising a plurality of liquid phase globules, wherein said generating of said liquid phase reaction component is configured to maximize a surface area value of said at least one exposed surface, and to minimize a thickness thereof; and
   (b) contacting an oxidizing agent, comprising oxygen with said at least one exposed surface of said liquid phase reaction component in said at least one non-barbotage process reactor to produce an oxidation output comprising a corresponding hydroperoxide,
   wherein said hydrocarbon is
   a compound of general formula $C_6H_5$-Alk, wherein Alk is a methyl, ethyl, n-propyl, iso-propyl, n-butyl, or sec-butyl group, or
   diisopropylbenzene.

2. The method of claim 1, further comprising at least one of the steps of:
   (c) contacting a reaction input comprising said hydrocarbon with said oxidizing agent in at least one barbotage process reactor to produce said liquid phase reaction component comprising said hydrocarbon and further comprising said corresponding hydroperoxide;
   (d) contacting said oxidation output further comprising said hydrocarbon with said oxidizing a ent in at least one barbotage process reactor to produce a product comprising said corresponding hydroperoxide; and
   (e) conducting oxidation of said product comprising said corresponding hydroperoxide and further comprising said hydrocarbon according to the method of claim 1,
   wherein said step (c) is conducted prior to said step (a),
   wherein said step (d) is conducted after said step (b), and
   wherein said step (e) is conducted after said step (d).

3. The method of claim 1, wherein said oxidizing agent comprises at least one of:
   air oxygen available in vicinity of said oxidation;
   a mixture of air oxygen and additional nitrogen added thereto; and
   a mixture of air oxygen and additional oxygen added thereto.

4. The method of claim 1, wherein said at least one non-barbotage process reactor comprises a collection region configured for collecting at least a portion of said oxidation output, said method further comprising:

(f) passing said oxidizing agent by way of a barbotage through said at least a portion of said oxidation output disposed in said collection region.

5. The method of claim 1, wherein said contacting is conducted at a temperature in a range from about 20° C. to about 150° C.

6. The method of claim 1, wherein said contacting is conducted under a pressure in a range from about 0.5 to about 15 atmospheres.

7. The method of claim 1, wherein said oxidization reaction is conducted isothermally.

8. The method of claim 1, wherein said oxidization is conducted adiabatically.

9. The method of claim 1, wherein said at least one non-barbotage process reactor is configured as a plurality of sequentially connected non-barbotage process reactors.

10. The method of claim 9,
wherein said oxidation is conducted isothermally in a portion of said sequentially connected non-barbotage process reactors, or
wherein said oxidation is conducted non-isothermally in a portion of said sequentially connected non-barbotage process reactors.

11. The method of claim 1,
wherein said oxidation output comprises at least one reaction inhibitor, and wherein said method further comprises:
(g) removing said at least one reaction inhibitor from said oxidation output by:
(1) washing said oxidation output with an alkaline agent; and
(2) returning said washed oxidation output to said at least one non-barbotage process reactor.

12. The method of claim 1, wherein said oxidation product comprises at least about 10 weight % of said corresponding hydroperoxides.

13. The method of claim 1, wherein said oxidation product comprises from about 5 weight % to about 85 weight % of said corresponding hydroperoxide.

14. The method of claim 1, wherein said hydrocarbon is cumene, and wherein said corresponding hydroperoxide is cumene hydroperoxide.

15. The method of claim 1, wherein said hydrocarbon is di-iso-propylbenzene, and wherein said corresponding hydroperoxide is di-iso-propylbenzene dihydroperoxide.

16. The method of claim 1, wherein said hydrocarbon is ethylbenzene, and wherein said corresponding hydroperoxide is ethylbenzene hydroperoxide.

17. The method of claim 1, wherein said hydrocarbon is sec-butylbenzene, and wherein said corresponding desired hydroperoxide is sec-butylbenzene hydroperoxide.

* * * * *